(12) United States Patent
Coustance et al.

(10) Patent No.: US 9,017,415 B2
(45) Date of Patent: Apr. 28, 2015

(54) PROSTHETIC ACETABULAR CUP IMPACTION PLATE

(71) Applicant: Stryker Ireland Ltd., Carrigtwohill (IE)

(72) Inventors: Antoine Coustance, Hérouville St Clair (FR); Loic Pinot, Blainville sur Orne (FR)

(73) Assignee: Stryker Ireland Ltd. (IE)

( * ) Notice: Subject to any disclaimer, the term of this patent is extended or adjusted under 35 U.S.C. 154(b) by 126 days.

(21) Appl. No.: 13/937,679

(22) Filed: Jul. 9, 2013

(65) Prior Publication Data
US 2014/0018933 A1  Jan. 16, 2014

(30) Foreign Application Priority Data
Jul. 10, 2012 (GB) .................... 1212247.9

(51) Int. Cl.
- A61F 2/32 (2006.01)
- A61F 2/34 (2006.01)
- A61F 2/46 (2006.01)
- A61F 2/30 (2006.01)

(52) U.S. Cl.
CPC .............. *A61F 2/34* (2013.01); *A61F 2/4609* (2013.01); A61F 2002/30322 (2013.01); A61F 2002/30326 (2013.01); A61F 2002/30617 (2013.01); A61F 2002/30708 (2013.01)

(58) Field of Classification Search
CPC ...... A61F 2/34; A61F 2/36; A61F 2220/0033
USPC .......................................... 623/22.11–22.39
See application file for complete search history.

(56) References Cited

U.S. PATENT DOCUMENTS

| | | | |
|---|---|---|---|
| 7,833,276 | B2 | 11/2010 | Auxepaules et al. |
| 2011/0130763 | A1 | 6/2011 | Aux Epaules et al. |
| 2012/0136360 | A1 | 5/2012 | Aux Epaules et al. |
| 2012/0136361 | A1 | 5/2012 | Aux Epaules et al. |

*Primary Examiner* — Jason-Dennis Stewart
(74) *Attorney, Agent, or Firm* — Lerner, David, Littenberg, Krumholz & Mentlik, LLP

(57) ABSTRACT

A prosthetic acetabular cup impaction plate comprising an annular cup engaging surface comprising an annular array of first shape portions adapted to substantially complement portions of the natural shape of the right side acetabulum, which first shape portions are intersected by an annular array of second shape portions adapted to substantially complement the natural shape of the left side acetabulum.

16 Claims, 3 Drawing Sheets

PROSTHETIC ACETABULAR CUP IMPACTION PLATE

CROSS-REFERENCE TO RELATED APPLICATION

The present application claims priority from Great Britain Patent Application No. GB 1212247.9 filed Jul. 10, 2012, the disclosure of which is hereby incorporated herein by reference.

BACKGROUND OF THE INVENTION

The present invention relates to a prosthetic acetabular cup impaction plate for use with a particular type of acetabular cup.

Prosthetic acetabular cup inserter and impactors are used to implant prosthetic acetabular cups into the cavity of a patient's hip, and generally comprise an elongate body with a cup engaging head at a first end thereof, and a handle and impaction anvil at a second end thereof. The surgeon releasably fits a cup implant to the cup engaging head, and then positions the cup inside the patient's hip. He then applies a hammering force to the impaction anvil to secure the cup in place, before releasing the cup from the cup engaging head.

In some cases the impaction force is imparted to the cup via an impaction plate provided at the cup engaging head. Such plates can comprise an annular cup engaging wall adapted to engage a rim of the cup such that the impaction force can be imparted thereto. Traditional acetabular cups are regular in shape, and comprise a rim in a single plane. An impaction plate suitable for use with such a cup construction would therefore comprise a cup engaging wall with an upper surface which is also in a single plane.

However, the peripheral rim of the natural acetabulum has a contoured shape and does not extend through a single plane. Considered perpendicular to the proximal/distal axis of the hip joint, the shape of the acetabular rim comprises three convex portions which extend between the ilium bone and the pubis bone, between the pubis bone and the ischium bone and between the ischium bone and the ilium bone. Of these three convex portions, that between the pubis and the ischium bones extends proximally to a greater extent than the other two. Further, the convex portion between the ilium and ischium bones is of a greater length than the other two. In addition, the intervening concave sections of the rim adjacent to the ischium and ilium bones extend distally to a greater extent than the remainder of the rim. As a result of this contoured shape, the angle of movement of the natural hip joint at certain positions of the femur is greater than that provided by a traditional prosthetic acetabular cup with a rim in a single plane. A further difficulty with such cups is that if they are not correctly positioned in the acetabulum, part of the rim can extend beyond the acetabulum. This can cause pain due to the rim conflicting with the psoas muscle which extends from the acetabulum to the femur, or with other muscles or tissues.

In order to solve some of the above problems U.S. Pat. No. 7,833,276 in the name of the applicant discloses a prosthetic acetabular cup with a rim shaped to mimic the contours of the natural shape of an acetabulum. The rim comprises spaced convex ilium, ischium and pubis portions, with concave portions in between. U.S. Pat. No. 7,833,276 also refers to an impaction plate comprising an annular cup engaging wall with an upper surface shaped to complement that of the rim of the cup. Such an impaction plate is shown more clearly in U.S. Patent Application Publication Nos. 20120136361, 20120136360 and 20110130763 in the name of the applicant. These applications relate to prosthetic acetabular cup inserter and impactors which are for use with acetabular cups such as shown in U.S. Pat. No. 7,833,276, and therefore may comprise impaction plates with annular cup engaging walls with a shape which complements that of the rim of the cup. The disclosure of U.S. Pat. No. 7,833,276 is incorporated herein by reference.

A problem with impaction plates with cup engaging surfaces shaped to complement the rims of acetabular cups designed to mimic the acetabulum, is that they are side specific. The natural shapes of the right and left acetabular rims mirror one another, but as the shapes are not symmetrical a cup designed to mimic the right acetabulum will not mimic the left. As a result, specific right and left hand side cups are provided, which necessitate specific right and left hand side impaction plates. The manufacture of side specific cups is not a particular problem, as a cup is required for each procedure in any case. However, the requirement for side specific impaction plates is a problem, because it adds a significant complication to the inserter and impactor tooling. Where in the past a single tool for repeated use in right and left side procedures could be provided, the side specific cups require either two separate side specific inserter and impactor tools, or a tool with interchangeable side specific impaction plates.

The present invention is intended to overcome some of the above problems.

BRIEF SUMMARY OF THE INVENTION

Therefore, according to a first aspect of the present invention, a prosthetic acetabular cup impaction plate comprises an annular cup engaging surface comprising an annular array of first shape portions adapted to substantially complement portions of the natural shape of the right side acetabulum, which first shape portions are intersected by an annular array of second shape portions adapted to substantially complement the natural shape of the left side acetabulum.

Thus, the present invention provides an impaction plate comprising a cup engaging surface with a shape partially complementary to the rim of a cup designed to mimic the right side acetabulum, and partially complementary to the rim of a cup designed to mimic the left side acetabulum. It can therefore support either. As the annular arrays of first and second shape portions intersect one another around the annular shape of the cup engaging surface, the loading in each case is spread around the rim of the cup during impaction, and is not concentrated in one area.

The shape of the cup engaging surface is based on the two opposite natural acetabular rim shapes being overlaid with one another on the same axis. This results in a symmetrical annular shape in which the various portions of the two annular arrays are defined from one another by the points at which the two acetabular rim shapes upon which they are based intersect one another.

As the natural acetabular rim shape is asymmetrical, the cup engaging surface can have different symmetrical shapes depending on the manner in which the two opposite natural acetabular rim shapes are rotationally aligned to form the shape of the cup engaging surface. For example, the pubis portions of the two opposite natural acetabular rim shapes can be arranged adjacent one another about the line of symmetry. However, given the particular contoured shapes of the two opposite natural acetabular rim shapes, it has been found that arranging the two opposite ilium portions adjacent one another about the line of symmetry is preferred. It results in the cup engaging surface comprising eight similarly sized and generally evenly distributed intersected portions. This shape of cup engaging surface is based on the two opposite natural acetabular rim shapes being overlaid with one another with an approximately 45 degree rotational divergence in each case from the natural proximal/distal axes of the hip joint. In other words, to align the two opposite ilium portions adjacent one another about the line of symmetry one natural acetabular rim shape is rotated approximately 45 degrees clockwise from a theoretical proximal/distal hip joint axes, while the other is rotated the same amount anti-clockwise in a mirror fashion.

Therefore, in a preferred embodiment the annular array of first shape portions can substantially complement portions of the natural shape of the right side acetabulum arranged at approximately 45 degrees in a first direction from a natural position on a proximal/distal axis of a right side hip joint, and the annular array of second shape portions can substantially complement portions of the natural shape of the left side acetabulum arranged at approximately 45 degrees in the opposite direction from a natural position on a proximal/distal axis of a left side hip joint.

This results in the cup engaging surface comprising eight similarly sized and generally evenly distributed intersected portions. This is beneficial because it spreads the impact loading in use as efficiently as possible around the rim of the acetabular cup. This particular configuration arises because the natural shape of the acetabular rim comprises three concave portions, being those adjacent the pubis, ilium and ischium bones, which are intersected by convex portions, with that between the ischium and the ilium bones being somewhat greater in circumferential extent than the others. As such, arranging the ilium portions adjacent one another about the line of symmetry results in these eight intersected portions because the closely aligned convex pubis and ischium portions of each rim shape intersect the wider concave inter ilium/ischium portion of the other.

Therefore, the cup engaging surface can comprise, in order, a first ilium portion, a second pubis portion, a first inter ilium/ischium portion, a second ischium portion, a first ischium portion, a second inter ilium/ischium portion, a first pubis portion and a second ilium portion.

The cup engaging surface can be formed into a front face of the impaction plate. However, in a preferred embodiment the impaction plate can comprise an annular cup engaging wall extending parallel to said lengthwise axis, and said cup engaging surface can comprise an upper surface of said cup engaging wall.

The impaction plate described above can be provided as a separate component, but it will be appreciated that in many cases it would be provided as a part of an acetabular cup inserter and impactor tool.

A prosthetic acetabular cup implantation system comprise right and left acetabular cups and an instrument with an impaction plate having an annular cup engaging surface comprising an annular array of first shape portions adapted to substantially complement portions of a right acetabular cup having a rim mimicking the natural shape of the right side acetabulum. The first shape portions are intersected by or alternate with an annular array of second shape portions adapted to substantially complement portions a left acetabular cup having a rim mimicking the natural shape of the left side acetabulum. The annular array of first shape portions substantially complement portions of the natural shape of the right side acetabulum arranged at approximately 45 degrees in a first direction from a natural position on a proximal/distal axis of a right side hip joint, and in which the annular array of second shape portions substantially complement portions of the natural shape of the left side acetabulum arranged at approximately 45 degrees in the opposite direction from a natural position on a proximal/distal axis of a left side hip joint. The cup engaging surface of the impaction plate comprises, in order, a first ilium portion, a second pubis portion, a first inter ilium/ischium portion, a second ischium portion, a first ischium portion, a second inter ilium/ischium portion, a first pubis portion and a second ilium portion. The impaction plate comprises an annular cup engaging wall extending parallel to a lengthwise axis thereof, and in which the cup engaging surface comprises an upper surface of the cup engaging wall.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The invention can be performed in various ways, but one embodiment will now be described by way of example, and with reference to the accompanying drawings, in which.

DETAILED DESCRIPTION

Figure 1:
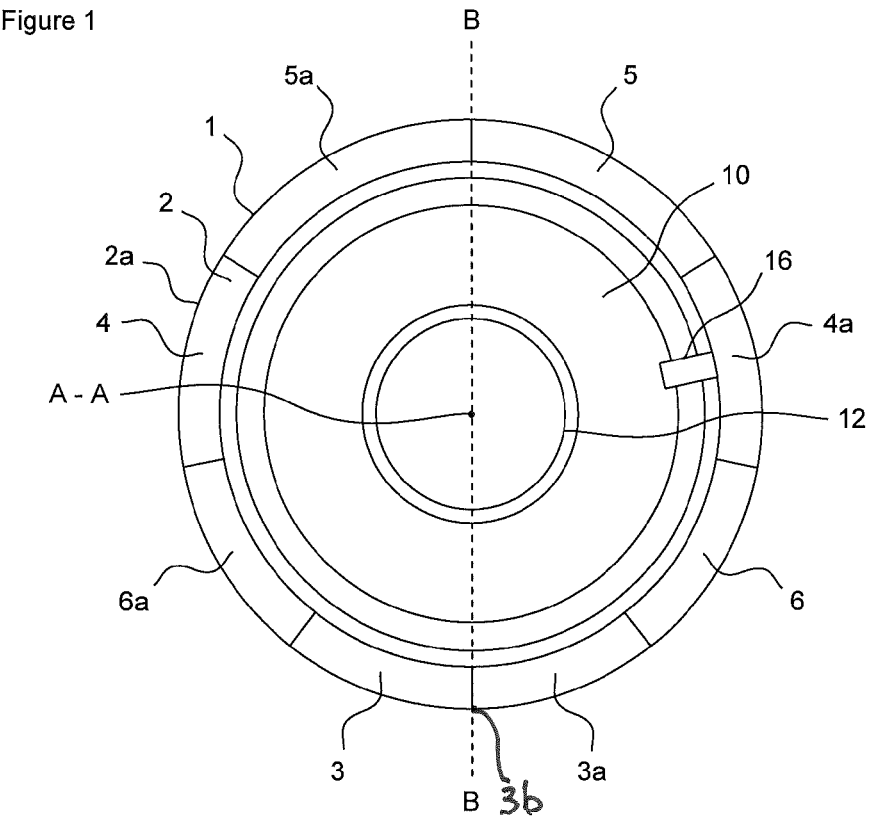
FIG. 1 is a top view of a prosthetic acetabular cup impaction plate according to the first aspect of the present invention.
Figure 2:
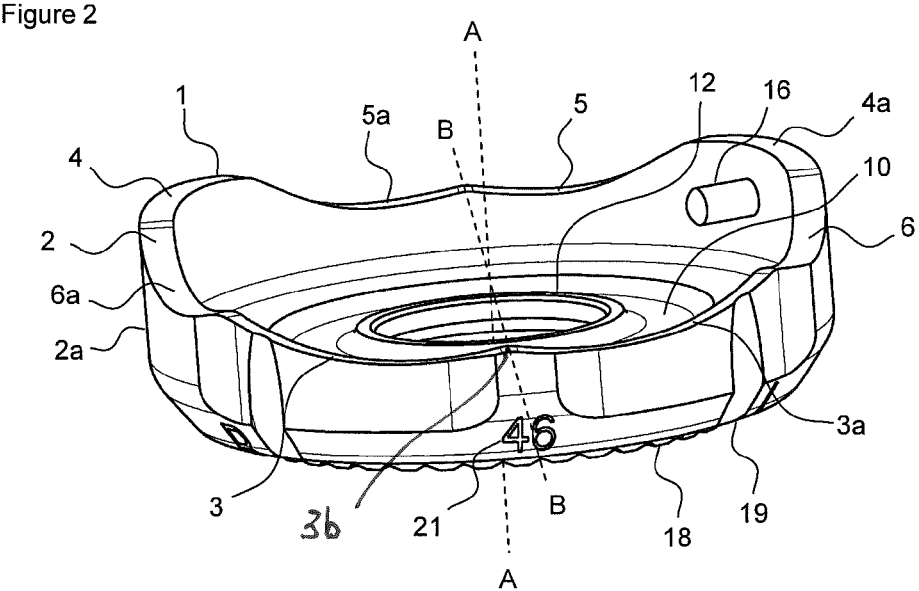
FIG. 2 is a perspective view of the prosthetic acetabular cup impaction plate as shown in FIG. 1.

As shown in FIGS. 1 and 2, a prosthetic acetabular cup impaction plate 1 comprises an annular cup engaging surface 2 comprising an annular array of first shape portions 3, 4, 5, and 6 adapted to substantially complement portions of the natural shape of the right side acetabulum. The first shape portions 3, 4, 5 and 6 are intersected by an annular array of second shape portions 3a, 4a, 5a, and 6a adapted to substantially complement the natural shape of the left side acetabulum.

Figure 5:
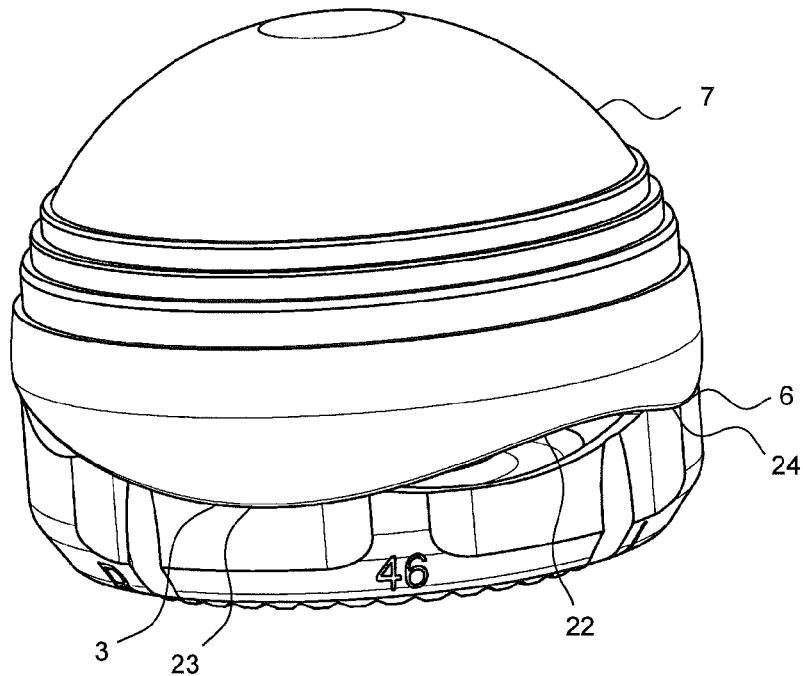
FIG. 5 is a perspective view of the prosthetic acetabular cup impaction plate as shown in FIG. 1 with a right side acetabular cup mounted thereon.
Figure 6:
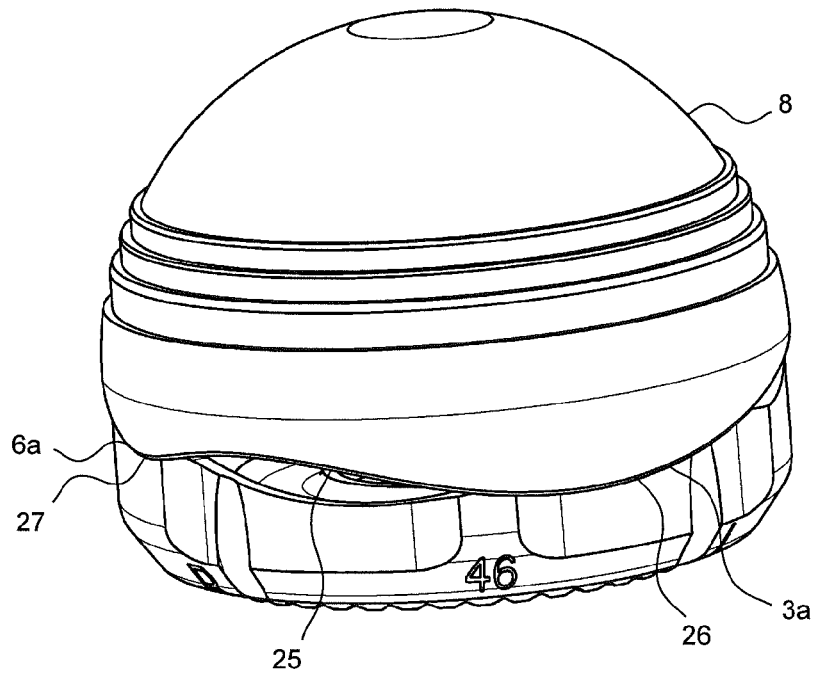
FIG. 6 is a perspective view of the prosthetic acetabular cup impaction plate with a left side acetabular cup mounted thereon.

The annular array of first shape portions 3, 4, 5 and 6 comprises a first ilium portion 3, a first inter ilium/ischium portion 4, a first ischium portion 5 and a first pubis portion 6. These serve to support the corresponding sections of a right side acetabular cup 7, as shown in FIG. 5. The annular array of second shape portions 3a, 4a, 5a and 6a comprises a second ilium portion 3a, a second inter ilium/ischium portion 4a, a second ischium portion 5a and a second pubis portion 6a. These serve to support the corresponding sections of a left side acetabular cup 8, as shown in FIG. 6.

As is clear from FIGS. 1 and 2, the annular array of first shape portions 3, 4, 5 and 6 and the annular array of second shape portions 3a, 4a, 5a and 6a are mirror representations of one another about a line 3b which is an axis of symmetry B-B.

The shape of the cup engaging surface 2 is based on the natural shapes of the right side acetabulum and the left side acetabulum being overlaid with one another while rotated approximately 45 degrees in opposite directions from natural positions on proximal/distal axes of the opposite hip joints. The lengthwise axis A-A is representative of such axes being aligned with one another.

Therefore, the cup engaging surface 2 comprises, in order around its circumference starting from the point 36 where it intersects the line of symmetry B-B at the lowest point in FIG. 1, and from point 36 which is closest to the viewer in FIG. 2, the first ilium portion 3, the second pubis portion 6a, the first inter ilium/ischium portion 4, the second ischium portion 5a, the first ischium portion 3, the second inter ilium/ischium portion 4a, the first pubis portion 6 and the second ilium portion 3a.

It will be appreciated that this particular symmetrical shape has been achieved by aligning the ilium portions 3 and 3a adjacent to one another about the axis of symmetry B-B (and on the opposite side the ischium portions 5 and 5a), and thereby separating the pubis portions 6 and 6a. Given the natural contoured shape of the acetabular rim with its three concave pubis, ilium and ischium portions, and with the convex inter ilium/ischium portion being greater in circumferential extent than the others, the result of aligning the ilium portions 3 and 3a about the line of symmetry B-B is that the closely aligned convex pubis and ischium portions of one acetabular rim shape interrupt the wide concave inter ilium/ischium portion of the other, leaving only the short portions 4 and 4a remaining. It will be appreciated from FIGS. 1 and 2 that the eight portions 3, 4, 5, 6, 3a, 4a, 5a, and 6a each have approximately the same circumferential extent (although the ischium portions 5 and 5a are slightly larger than the others), and this is deliberate because it spreads the impact loading in use as efficiently as possible around the rim of the acetabular cup 7 or 8.

If the corresponding right and left side acetabular rim shapes which determine the shape of the surface 2 were aligned symmetrically at a different rotational relationship to one another, then the resulting annular arrays of first and second shape portions would not be so evenly sized and distributed about the surface 2.

As shown in FIG. 2, the impaction plate 1 comprises an annular cup engaging wall 2a extending parallel to the lengthwise axis A-A. The cup engaging surface 2 comprises an upper surface of the wall 2a.

Figure 3:
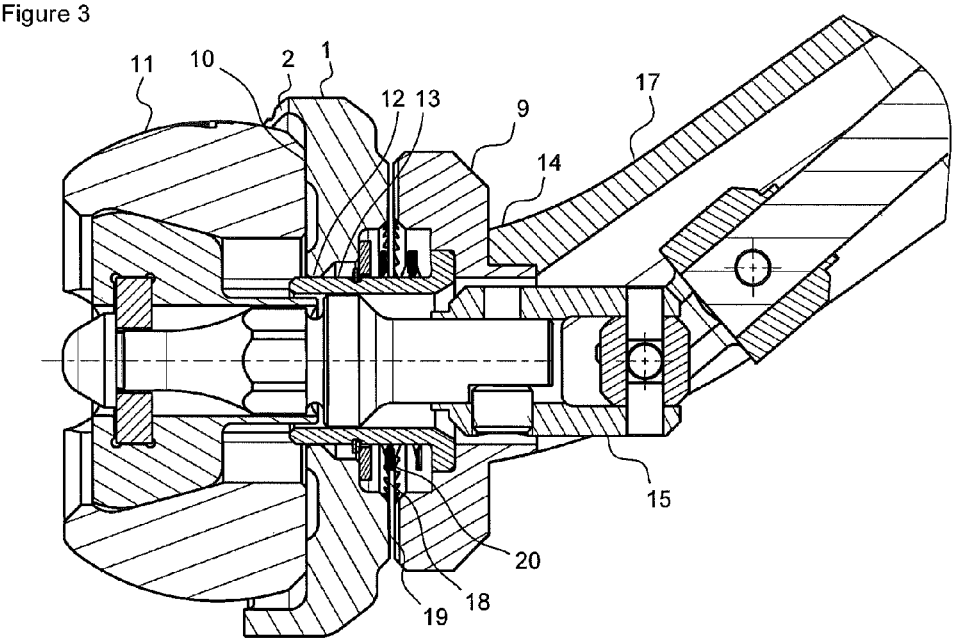
FIG. 3 is a partial cross-sectional view of an acetabular cup inserter and impactor according to the second aspect of the present invention.
Figure 4:
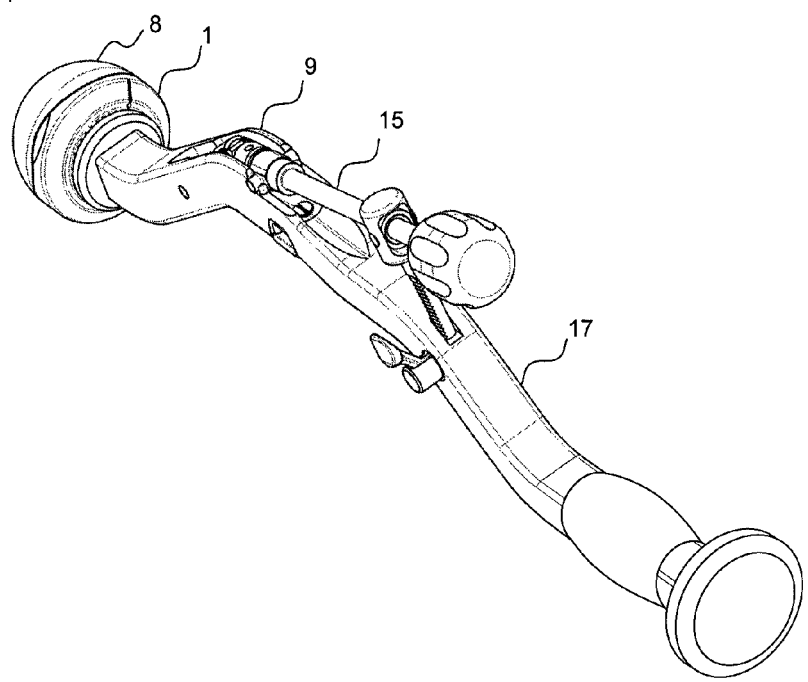
FIG. 4 is a perspective view of the acetabular cup inserter and impactor as shown in FIG. 3.

The impaction plate 1 comprises a number of other features pertaining to its use as a part of an acetabular cup inserter and impactor 9 like that described in the applicant's co-pending patent applications published as U.S. 20120136360 and 20120136361, the disclosures of which are incorporated herein by reference, which is shown in FIGS. 3 and 4. In particular, the plate 1 comprises a front face 10, which is adapted to support a resilient ring 11 which is biased radially outwardly in use to engage the inner surface of an acetabular cup 7 or 8, and hold it in place on the wall 2a. The plate 1 also comprises a central aperture 12, which allows it to be mounted on a sleeve component 13 at the operative end 14 of the inserter and impactor 9. This manner of mounting the impaction plate 1 on the inserter and impactor 9 allows for its easy disassembly therefrom. A linkage 15, passes through the sleeve component 13 and acts to bias the resilient ring 11 supported on the front face 10 radially outwardly in use.

A radially inwardly extending spigot 16 is provided on the wall 2a, which is for rotational engagement with a slot (not visible) provided on the resilient ring 11. This allows for axial rotation imparted to the resilient ring 11 in use by the linkage 15 to be transmitted to the plate 1. Rotation of the cup 7 or 8, resilient ring 11 and plate 1 in relation to the body 17 of the inserter and impactor 9 is a feature of the invention in the applicant's co-pending patent application. In addition, an annular set of teeth 18 is provided on a rear face 19 of the impaction plate 1, which form a part of releasable locking means along with a corresponding set of teeth 20 provided on the body 17 of the inserter and impactor 9. Engagement of the sets of teeth 18 and 20 in use serves to lock the plate 1, the resilient ring 11 and the acetabular cup 7 or 8 against rotation, once a desired rotational position thereof in relation to the body 17 of the inserter and impactor 9 has been reached. Reference is made to the applicant's co-pending patent applications for a full explanation of the features and workings of the inserter and impactor 9. The impaction plate 1 also carries indicia 21, which pertain to its particular size and/or purpose.

Therefore, in use the impaction plate 1 is assembled as part of the inserter and impactor 9. Depending on the procedure to be performed, either the right side cup 7, or left side cup 8 is applied to the wall 2a of the impaction plate 1, as shown in FIG. 5 or 6 respectively. The rim 22 of the right side cup 7 comes into contact with the annular array of first shape portions 3, 4, 5 and 6, and is therefore supported at its ilium portion 23, at an inter ilium/ischium portion (not visible), its ischium portion (not visible) and its pubis portion 24. The rim 25 of the left side cup 8 comes into contact with the annular array of second shape portions 3a, 4a, 5a and 6a, and is therefore supported at its ilium portion 26, at an inter ilium/ischium portion (not visible), its ischium portion (not visible) and its pubis portion 27.

The linkage means 15 is then operated to radially outwardly expand the resilient ring 11, which holds the cup 7 or 8 in place on the inserter and impactor 9. FIG. 4 shows the left side cup 8 engaged on the inerter and impactor 9 in this way. The linkage means 15 is then operated again to set a preferred rotational position of the cup 7 or 8 in relation to the body 17 of the inserter and impactor 9. The linkage 15 is then operated once again to engage the teeth 18 and 20 to lock the impaction plate 1 in position in relation to the body 17 of the inserter and impactor 9.

The cup 7 or 8 is then offered up to the patient's acetabulum, with the lengthwise axis A-A of the impaction plate 1 substantially aligned with a proximal/distal axis of the acetabulum, and the cup engaging surface 2 therefore arranged in an anterior/posterior position of the patient. Rotation of the impaction plate 1 about its lengthwise axis A-A, either via the linkage means 15, or via rotation of the whole inserter and impactor 9, can then be performed to rotationally align the rim 22 or 25 of the cup 7 or 8, with the natural shape of the acetabular rim.

Once in place an impaction force is imparted to the cup 7 or 8 via the inserter and impactor 9 to secure it in place in the acetabulum. This is transmitted to the cup 7 or 8 through the wall 2a and the cup engaging surface 2, and in particular the annular array of first or second shape portions 3, 4, 5 and 6 or 3a, 4a, 5a, and 6a. As explained above, this loading is substantially evenly distributed around the rim 22 or 25 of the cup 7 or 8 by virtue of the generally equally sized and distributed shape portions 3, 4, 5 and 6 or 3a, 4a, 5a and 6a of each array respectively. This prevents the occurrence of any high pressure points which might cause damage to the cup 7 or 8.

Once the cup 7 or 8 is fitted in place in the acetabulum the linkage 15 is operated to remove the radial outward biasing of the resilient ring 11, which allows the cup 7 or 8 to be released from the inerter and impactor 9, and for the inserter and impactor 9 to then be removed from the patient.

Therefore, it will be appreciated that the same impaction plate 2 can be used to fit either a right or a left side acetabular cup 7 or 8, which means that the inserter and impactor 9 can be used as shown in FIGS. 3 and 4 for either procedure. There is no need to have two separate side-specific impaction plates, which have to be fitted accordingly.

The second aspect of the present invention provides a prosthetic acetabular cup inserter and impactor comprising an impaction plate as shown in FIGS. 3 and 4.

The invention can be altered without departing from the scope of the claims. For example, in alternative embodiments (not shown) the two acetabular rim shapes which form the basis for the shape of the cup engaging surface are misaligned with one another on the lengthwise axis of the plate. This results in the annular array of first shape portions and the annular array of second shape portions being quite different from one another, and the cup engaging surface having an asymmetrical shape.

In further alternative embodiments (not shown) cup impaction plates have cup engaging surfaces with different symmetrical shapes to that shown in the embodiment above. The shapes depend on the manner in which the two opposite natural acetabular rim shapes are rotationally aligned to form the cup engaging surface. As such, in these alternative embodiments other portions than the ilium portions are arranged adjacent one another on either side of the line of symmetry, for example the opposite pubis portions.

In another alternative embodiment (not shown) the cup engaging surface is formed in the front face of the impaction plate, and not at the top of a wall provided thereon.

In further alternative embodiments impaction plates are provided with alternative means for fitment to an inserter and impactor, for example screw threads. In addition, in an alternative embodiment of the second aspect of the present invention, an inserter and impactor is provided with an impaction plate which is integral rather than a removable part.

Therefore, the present invention provides an impaction plate which is shaped to support cups designed to mimic both the left and the right side acetabulum. Half of the total area of the cup engaging surface engages one kind of cup in use, while the other half engages the other. This prevents the need to provide separate side-specific impaction plates.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic acetabular cup implantation system comprising a left and a right side acetabular cup each having an anatomically shaped rim; and an impaction plate having an annular cup engaging surface comprising an annular array of first shape portions adapted to substantially complement portions of the anatomical shape of the right side acetabular cup rim, which first shape portions are intersected by an annular array of second shape portions adapted to substantially complement portions of the natural shape of the left side acetabular cup rim.

2. The prosthetic acetabular cup implantation system claimed in claim 1 in which the impaction plate annular array of first shape portions substantially complement portions of the anatomical shape of the right side acetabular cup rim arranged at approximately 45 degrees in a first direction from a natural position on a proximal/distal axis of a right side hip joint, and in which the annular array of second shape portions substantially complement portions of the anatomical shape of the left side acetabular cup arranged at approximately 45 degrees in the opposite direction from a natural position on a proximal/distal axis of a left side hip joint.

3. The prosthetic acetabular cup implantation system as claimed in claim 2 in which the impaction plate has a cup rim engaging surface comprising in order, a first ilium portion, a second pubis portion, a first inter ilium/ischium portion, a second ischium portion, a first ischium portion, a second inter ilium/ischium portion, a first pubis portion and a second ilium portion shaped to engage portions of both the rims of the left and right side acetabular cups.

4. The prosthetic acetabular cup implantation system as claimed in claim 1 in which the impaction plate comprises an annular acetabular cup rim engaging wall extending parallel to a lengthwise axis thereof, and in which the acetabular cup rim engaging surface comprises an upper surface of said cup engaging wall.

5. The prosthetic acetabular cup implantation system as set forth in claim 1 wherein the impaction plate rim has a plurality of first contour portions engagable with the right acetabular cup and a plurality of second contour portions engageable with the left acetabular cup, the first and second contour portions alternating around a circumference of the impaction plate.

6. The prosthetic acetabular cup implantation system as set forth in claim 5 wherein there are four (4) first contour portions and four (4) second contour portions.

7. The prosthetic acetabular cup impaction system as set forth in claim 6 wherein the four first and second rim contour portions each encompass 45° of the 360° circumference of the impaction plate.

8. A prosthetic acetabular cup implantation system comprising:

a left and right acetabular cup each having an outer member including an outer surface, said outer member having a part-spherical inner bearing surface, the outer member extending about a polar axis terminating in a 360 degree circumferential distal rim surrounding the opening of the acetabulum, the rim having a generally inferiorly facing edge surface, the polar axis is perpendicular to a plane containing the rim of the acetabulum, the generally inferiorly facing edge surface of the rim of the outer member having a contour continuously curved in the generally inferior-superior direction around the entire circumference of the rim with the generally inferiorly facing edge surface moving toward and away from the plane of the acetabular rim two times such that a portion of the generally inferiorly facing edge surface of the rim to be located between the ischium and the pubis extends further towards a polar region of the bearing surface where the polar axis intersects the bearing surface than a contour portion of the generally inferiorly facing edge surface of the rim to be implanted between the pubis and the ilium and a generally inferiorly facing edge surface contour portion to be implanted between the ischium and the ilium and a contour portion of the generally inferiorly facing edge surface of the rim to be implanted between the pubis and the ilium extends distally further from the polar region than the contour of the generally inferiorly facing edge surface of the rim between the ischium and the ilium, wherein the contours of the outer edge of the rim to be implanted at the ischium and the ilium are closer to the polar region than the remainder of the rim, the contour portions of the right and left cup being circumferentially offset from one another;

an impactor plate comprising a rim having surface portions adapted to engage the offset contour portions of the generally inferiorly facing edge surface of the rim of both the right and left acetabular cups.

9. The prosthetic acetabular cup implantation system as claimed in claim 8 in which the impactor plate rim offset contour portions have first shaped portions substantially complementary portions of the shape of the right acetabular cup rim, the first shaped portions arranged at approximately 45 degrees in a first direction from a natural position on a proximal/distal axis of a right side hip joint, and the impaction plate rim has second contour portions substantially complementary to contour portions of the shape of the left acetabular cup rim arranged at approximately 45 degrees in a second opposite direction from a natural position on a proximal/distal axis of a left side acetabulum.

10. The prosthetic acetabular cup implantation system as claimed in claim 9 in which the impactor plate cup engaging rim contour portions comprises, in order, a first ilium portion, a second pubis portion, a first inter ilium/ischium portion, a second ischium portion, a first ischium portion, a second inter ilium/ischium portion, a first pubis portion and a second ilium portion.

11. The prosthetic acetabular cup implantation system as claimed in claim 8 in which the impaction plate comprises an annular cup engaging wall extending parallel to a lengthwise axis thereof, and in which said cup engaging rim contour portions comprises an upper surface of said cup engaging wall.

12. The prosthetic acetabular cup implantation system as set forth in claim 8 wherein the impaction plate rim has a plurality of first offset contour portions engagable with the right acetabular cup and a plurality of second offset contour portions engageable with the left acetabular cup, the first and second contour portions alternating around a circumference of the impaction plate.

13. The prosthetic acetabular cup implantation system as set forth in claim 12 wherein there are four (4) first contour portions and four (4) second contour portions.

14. The prosthetic acetabular cup implantation system as set forth in claim 13 wherein the four first and second offset contour portions each encompass 45° of the 360° circumference of the impaction plate.

15. The prosthetic acetabular cup implantation system as claimed in claim 14 in which the cup engaging rim contour portion comprises, in order, a first ilium portion, a second pubis portion, a first inter ilium/ischium portion, a second ischium portion, a first ischium portion, a second inter ilium/ischium portion, a first pubis portion and a second ilium portion.

16. The prosthetic acetabular cup implantation system as claimed in claim 15 in which the impaction plate comprises an annular cup engaging wall extending parallel to a lengthwise axis thereof, and in which said cup engaging rim contour portions comprises an upper surface of said cup engaging wall.

* * * * *